United States Patent [19]
McLees

[11] Patent Number: 5,135,504
[45] Date of Patent: Aug. 4, 1992

[54] NEEDLE TIP GUARD

[76] Inventor: Donald J. McLees, 2623 Virginia Ave., Everett, Wash. 98201

[21] Appl. No.: 381,093

[22] Filed: Jul. 17, 1989

[51] Int. Cl.⁵ .............................................. A61M 5/178
[52] U.S. Cl. .................................... 604/164; 604/263
[58] Field of Search ............... 604/110, 162, 164, 166, 604/167, 168, 198, 263, 52, 53; 128/919

[56] References Cited

U.S. PATENT DOCUMENTS

| | | | |
|---|---|---|---|
| 3,904,033 | 9/1975 | Haerr | 604/263 X |
| 4,573,981 | 3/1986 | McFarlane | 604/263 |
| 4,610,671 | 9/1986 | Luther | 604/168 |
| 4,762,516 | 8/1988 | Luther et al. | 604/164 |
| 4,781,692 | 11/1988 | Jagger et al. | 604/164 |
| 4,846,805 | 7/1989 | Sitar | 604/165 |
| 4,850,961 | 7/1989 | Wanderer et al. | 604/53 |
| 4,911,694 | 3/1990 | Dolan | 604/198 |
| 4,929,241 | 5/1990 | Kulli | 604/263 |
| 4,932,945 | 6/1990 | Braginetz et al. | 604/195 |
| 4,935,012 | 6/1990 | Magre et al. | 604/192 |
| 4,944,728 | 7/1990 | Carrell et al. | 604/164 |
| 4,952,207 | 8/1990 | Lemieux | 604/164 |
| 4,964,854 | 10/1990 | Luther | 604/166 |
| 4,966,587 | 10/1990 | Baumgart | 604/164 |
| 4,973,317 | 11/1990 | Bobrove | 604/198 |
| 4,995,866 | 2/1991 | Amplatz et al. | 604/53 |

Primary Examiner—C. Fred Rosenbaum
Assistant Examiner—Mark O. Polutta

[57] ABSTRACT

A guard for the tip of an intravenous needle which operates automatically when the needle is withdrawn from an intravenous catheter.

1 Claim, 2 Drawing Sheets

NEEDLE TIP GUARD

BACKGROUND OF THE INVENTION

1. Field of the Invention

This invention relates to medical instruments. It applies specifically to medical needles used for placing an intravenous catheter into a vein. In the U.S. Patent Office it would be found in a classification for needle tip guards which protect health care workers from accidental needle sticks.

2. Description of the Prior Art

To help prevent health care workers from becoming infected by hepatitis or AIDS or the like from an accidental needle prick, it would be desirable to have a guard which covers the tip of an intravenous needle after use. Many such guards have been previously disclosed for hypodermic needles and syringes in general, but no guard has yet been manufactured specifically when the needle is withdrawn from the catheter.

Generally one of the first steps of an emergency medical procedure or a surgical operation is to insert a catheter into the patient's vein so that plasma, anesthetics, or other medications may be conveniently administered. Typically this involves first inserting a needle and plastic catheter combination and then removing the needle to leave only the plastic catheter in the vein. The possibly contaminated needle must then be further handled and disposed of. Obviously it would be desirable to have a guard automatically enclose the sharp end of the needle when it is withdrawn from the catheter, thus preventing the possibility of infection from an accidental needle prick during subsequent handling.

Vaillancourt (U.S. Pat. No. 4,725,267) shows some needle guards which protect the end of a needle after use, but they are not entirely automatic since a mechanism must be pushed or turned to initiate their operation. Also, they are not intended for use with a catheter.

Jagger, Pearson, and Guyenet (U.S. Pat. No. 4,781,692) show a novel solution to the intravenous needle problem. In their invention the needle is withdrawn from the end of the catheter which is in the vein, but remains inside the catheter tubing. Thus the possibly infected needle need not be dealt with and is simply thrown away with the rest of the catheter apparatus after use. However, relative to a simple plastic catheter and fitting, this leaves a more complex and bulky apparatus attached to the patient which can be very uncomfortable and more difficult to handle. The needle left inside can restrict flow of the fluid to the patient.

SYMMARY OF THE INVENTION

It is an object of this invention to provide a very simple and inexpensive guard for the tip of an intravenous catheter needle which does not significantly increase the size of the catheter or affect its ease of operation. It is a further object of this invention to provide such a guard which operates entirely automatically and thus requires no further action from the operator beyónd the normal insertion and withdrawal of the needle.

In order to satisfy the objects of the invention and improve upon the prior art, a simple needle tip guard has been devised which in its initial position resides entirely inside the hub of a standard catheter. The needle initially passes completely through the guard. The presence of the needle keeps the end of the guard flared out and thereby retained inside the hub until the needle is withdrawn from the catheter. At that time a slightly widened portion of the needle tip catches the guard, forcing the end of the guard to close over the tip and pulling the guard from the hub.

DETAILED DESCRIPTION OF THE DRAWINGS

Figure 1:
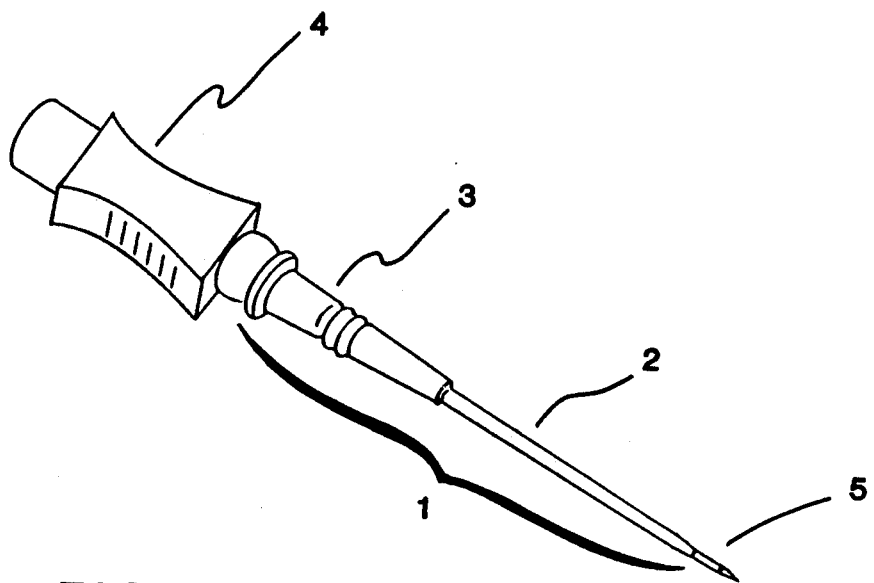
FIG. 1 shows the needle and catheter together.

In FIG. 1 the combined needle and catheter assembly is shown as it would normally appear before use. The plastic portion 1 remains with the patient after the needle is withdrawn and comprises a then flexible catheter tube 2 and its attached fluid fitting 3. The plastic handle 4 is attached to the needle 5. The distal end of the needle 5 can be seen protruding from the catheter 2 which includes a tapered end to ease insertion. The handle and the attached needle are pulled out of the catheter and its fitting after insertion into a vein, leaving the fitting protruding outwardly from the patient.

Figure 2:
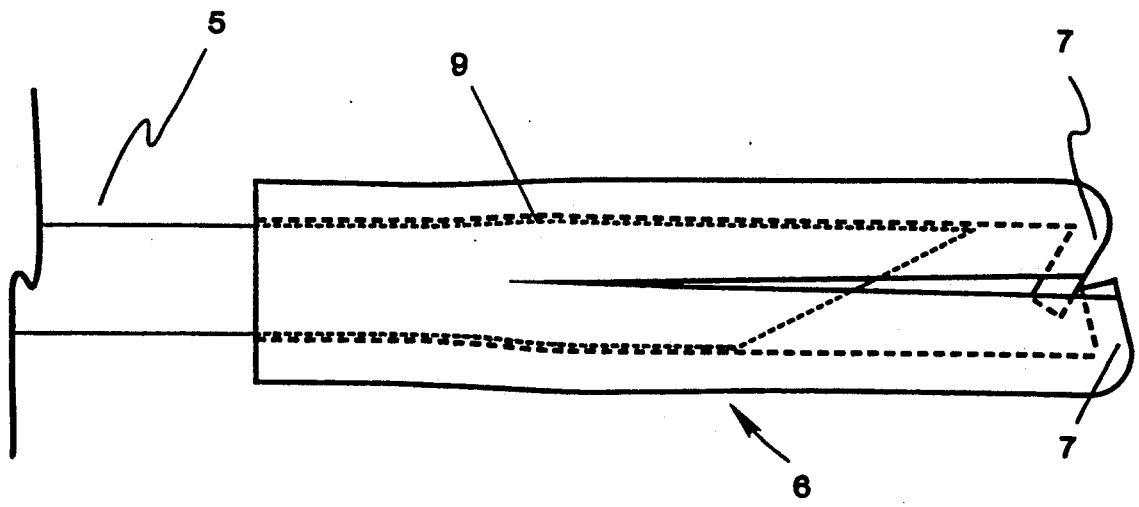
FIG. 2 is an enlarged side view of the preferred embodiment of the guard.

The preferred embodiment of the guard 6 is shown in FIG. 2. Here the guard is seen in its position over the end of the needle 5 as it would appear after the needle has been withdrawn. In this embodiment the guard is a hollow cylinder with a split end and slanted overlapping end caps 7. The guard can be made of any suitable material such as metal or plastic which is strong enough to contain the sharp metal needle tip and has memory such that it can spring back substantially to its original shape after the end has been flared open by the shaft of the needle prior to insertion. Also to be seen in this view is that the needle end has a larger diameter forming a shoulder 9.

Figure 3:
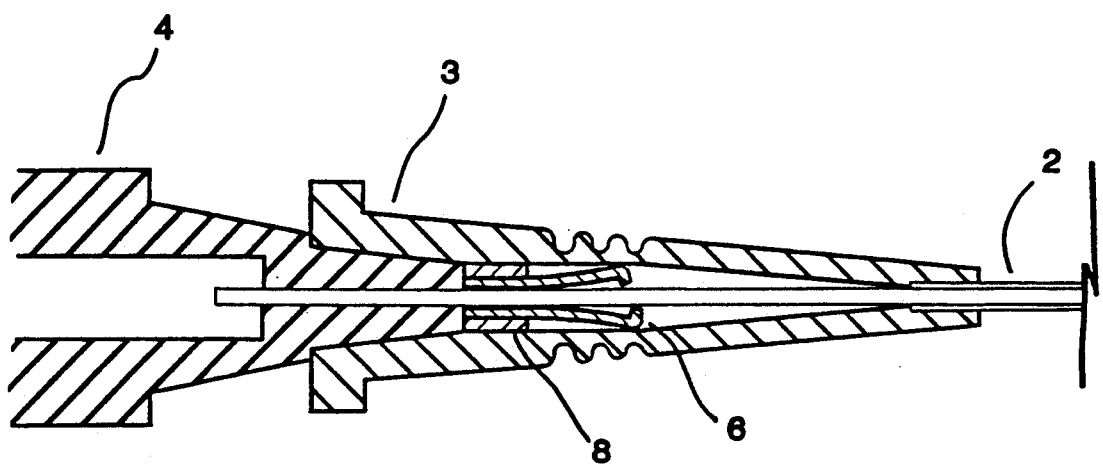
FIG. 3 is a side view cross sectional drawing of the needle, catheter and guard together.

The operating mechanism of the guard can be seen in the cross section of FIG. 3. Here the guard 6 appears in its position prior to needle withdrawal. A retaining ring 8 is held tightly by a friction fit with the catheter fluid fitting 3. The outside diameter of the guard is less than the inside diameter of the ring 8 so that normally the guard can easily slide through the ring. The needle shaft flares out the end of the guard displacing the end caps outward into the larger internal diameter portion of the hub and the guard is therefore prevented from moving by the retaining ring as the needle is withdrawn. The distal end of the needle 5 is flared out and is slightly larger in diameter than the inside diameter of the guard. When the needle is withdrawn and the tip goes inside the guard, the guard end caps are free to close. The flared out needle tip shoulder 9 pulls the guard through the retaining ring thus forcing the flared end of the guard closed.

It can be noted that the slightly flared needle tip does not hinder insertion into the vein. As a matter of fact positioning the catheter end just behind the shoulder 9 can help eliminate the usual catheter bulge.

Figure 4:
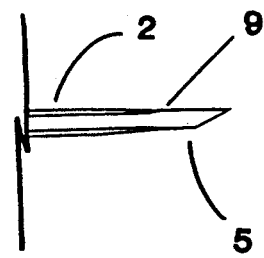
FIG. 4 shows the needle with the guard in place at the tip after removal from the catheter.
Figure 4:
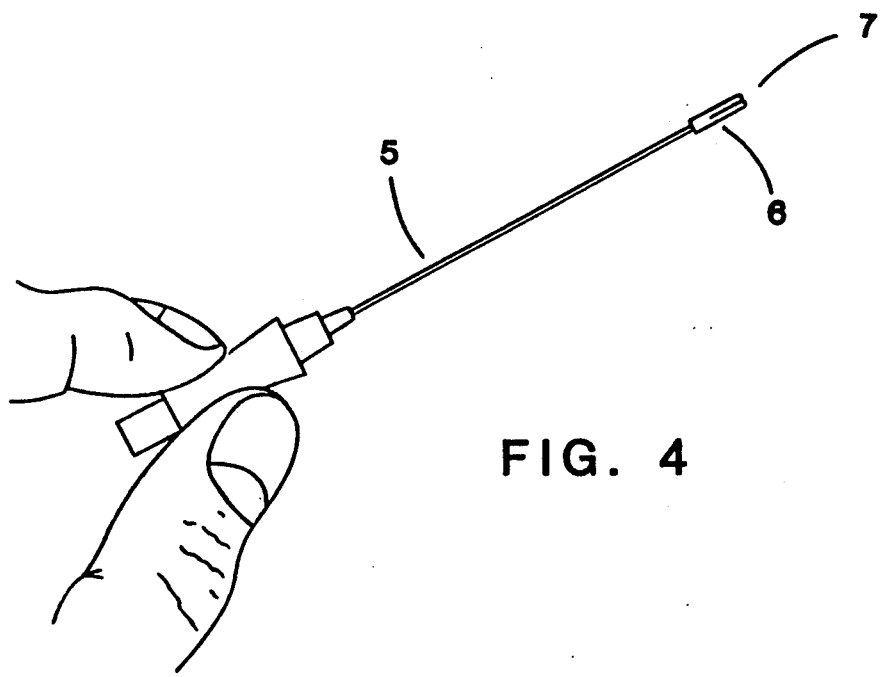

The needle 5 and guard 6 are shown after needle withdrawal from the catheter fitting in FIG. 4. The guard has been activated automatically by the withdrawal of the needle and cannot be pulled off the end of the needle because of the shoulder and the guard cannot slide down the shaft or be penetrated by the needle tip because the tip is contained by the inwardly slanting and overlapping guard ends 7.

What is claimed is:

1. An intravenous catheter insertion kit and a needle guard comprising:

a flexible catheter and its attached hub;

an insertion needle assembly, the insertion needle having a slightly flared distal tip such that the needle diameter at said tip is slightly larger than the uniform diameter proximal of said tip; and a cylindrical needle tip guard captured within said hub and through which said needle passes, said guard being made of a material having shape retaining memory and said guard having a split end with end caps, said end caps being displaced outward from the axis of the needle by the needle surface and said end caps being closeable by said shape retaining memory to a position containing the needle tip upon entry of the needle tip into said needle tip guard, said hub having an enlarged internal diameter at said guard end caps large enough to allow displacement of the end caps away from the needle axis by the needle surface and said hub also having an internal diameter proximal of said enlarged diameter which is too small to allow passage of said end caps in their displaced out position but large enough to allow passage of said guard with said end caps in their closed position, and said guard having an inside diameter proximal of said displaced end caps smaller than said enlarged needle diameter whereby said enlarged needle diameter captures said needle tip guard and the needle tip becomes enclosed by said guard when said needle is withdrawn from said hub and catheter.

* * * * *